(12) United States Patent
Lidor-Hadas et al.

(10) Patent No.: US 6,201,148 B1
(45) Date of Patent: Mar. 13, 2001

(54) PROCESS FOR PREPARING ALENDRONIC ACID

(75) Inventors: Ramy Lidor-Hadas, Kfar Saba; Revital Lifshitz, Herzlia, both of (IL)

(73) Assignee: Teva Pharmaceuticals Industries, Ltd., Petach Tiqva (IL)

( * ) Notice: Subject to any disclaimer, the term of this patent is extended or adjusted under 35 U.S.C. 154(b) by 0 days.

(21) Appl. No.: 09/556,091

(22) Filed: Apr. 21, 2000

Related U.S. Application Data

(63) Continuation of application No. 09/251,634, filed on Feb. 17, 1999, now abandoned.

(51) Int. Cl.$^7$ .................................................. C07F 9/38
(52) U.S. Cl. .................... 562/13; 562/11; 562/8
(58) Field of Search ........................ 562/8, 11, 13

(56) References Cited

U.S. PATENT DOCUMENTS

| | | | |
|---|---|---|---|
| 4,407,761 | * | 10/1983 | Blum et al. . |
| 4,705,651 | * | 11/1987 | Staibano . |
| 5,159,108 | * | 10/1992 | Kieczkowski ......................... 562/12 |
| 5,908,959 | * | 6/1999 | Kubela et al. ......................... 562/13 |

FOREIGN PATENT DOCUMENTS

2248063 * 3/1992 (GB) .

OTHER PUBLICATIONS

CA:124:117423 abs of J Org Chem by Kieczykowski et al 60(25) pp. 8310–8312, 1995.*
CA:124:104537 abs of Supramol Chem by Leroux et al 5(4) pp. 267–272, 1995.*
CA:129:202991 abs of Zhongguo Yiyao Gongye Zazhi Bianjibu by Jiao et al 29(5) pp. 202–203, 1998.*

\* cited by examiner

*Primary Examiner*—Jean F. Vollano
(74) *Attorney, Agent, or Firm*—Kenyon & Kenyon

(57) ABSTRACT

A novel process for the preparation of alendronic acid is disclosed. The method comprises the steps of reacting a compound of formula I with $H_3PO_3$

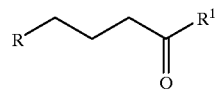

wherein R is an imido group and $R^1$ is selected from the group consisting of chloro, bromo, iodo, fluoro, hydroxy, amino, —$OR^2$ or —$OC(O)R^2$, wherein $R^2$ is $C_1$–$C_{12}$ alkyl, $C_1$–$C_{12}$ cycloalkyl or $C_1$–$C_{12}$ aryl; and then reacting the product of the first step with a deprotecting agent. Alendronic acid is then recovered. The method is safe, efficient and suitable for use on a large scale.

22 Claims, No Drawings

PROCESS FOR PREPARING ALENDRONIC ACID

This application is a continuation of Ser. No. 09/251,634, filed Feb. 17, 1999, now abandoned.

FIELD OF THE INVENTION

The present invention relates to new chemical processes for manufacturing bisphosphonic acids, and in particular for manufacturing alendronic acid.

BACKGROUND OF THE INVENTION

Alendronate sodium, 4-amino-1-hydroxybutylidene-1,1-bisphosphonic acid monosodium, having the formula

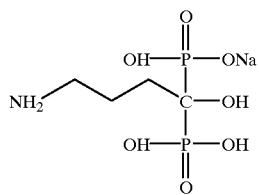

is an agent for combating bone resorption in bone diseases including osteoporosis and Paget's disease.

Various methods for preparing 4-amino-1-hydroxybutylidene-1,1-bisphosphonic acid, or alendronic acid, are known in the art and have been disclosed in M. I. Kabachnik et al., Synthesis and Acid-Base and Complexing Properties of Amino-Substituted alpha-hydroxylakylidene-diphosphonic Acids, Izu. Akad. Nauk USSR, Ser. Khim, 2,433 (1978) and in U.S. Pat. Nos. 4,407,761, 4,621,077, 4,705,651, 5,039,819 and 5,159,108.

A well known process for preparing alendronic acid is as follows (see also e.g. GB 2118042):

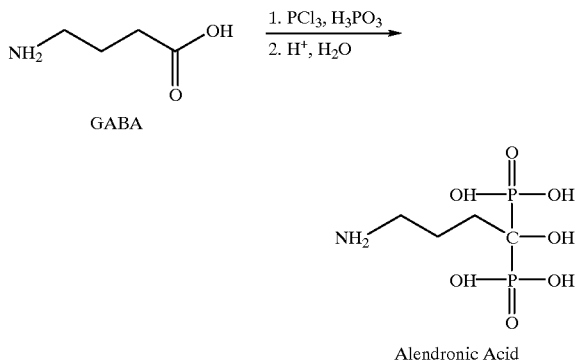

It has been reported that a solidification problem occurs when this process is performed on a large scale. The abbreviation GABA is defined hereinafter as 4(gamma)-aminobutyric acid.

U.S. Pat. No. 4,922,007 describes the preparation of alendronate sodium in trihydrate form, wherein 4-aminobutyric acid is reacted with phosphorous acid and phosphorous trichloride in the presence of methanesulfonic acid followed by the addition of sodium hydroxide. However, it has been reported that methanesulfonic acid reacts with the phosphorus trichloride and under adiabatic conditions the reaction becomes self-heating at 85° C., and an uncontrolled exotherm occurs at >140° C.

WO 98/34940 describes a process for preparing alendronic acid, which comprises reacting 4-aminobutyric acid with phosphorous acid and phosphorous trichloride in the presence of polyalkylene(glycol). However, it was reported that large quantities of polyalkylene(glycol) as well as toluene participate in this reaction, which renders it inefficient on a large scale.

Thus, there remains a need for a homogeneous, safe and efficient process for preparing alendronic acid.

SUMMARY OF THE INVENTION

The present invention relates to a novel process for preparing of alendronic acid, which comprises the steps of:

a) reacting a compound of the formula I with $H_3PO_3$

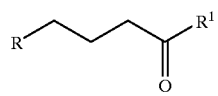

I wherein
R is an imido group; and
$R^1$ is selected from the group which consists of chloro, bromo, iodo, fluoro, hydroxy, amino, $-OR^2$ or $-OC(O)R^2$, wherein $R^2$ is $C_1-C_{12}$ alkyl, $C_1-C_{12}$ cycloalkyl, or $C_1-C_{12}$ aryl;

b) reacting the product of step (a) with a deprotecting agent; and c) recovering alendronic acid.

R is preferably selected from the group which consists of N-phthalimido and N-maleimido.

$R^1$ is preferably selected from the group which consists of chloro, bromo and hydroxy.

Optionally, the reaction of step (a) may be assisted with one or more of the compounds selected from the group which consists of $H_3PO_4$, $PCl_3$, $PCl_5$ and $POCl_3$.

The deprotecting agent of step (b) may be a non-oxidizing acid, preferably selected from the group which consists of HCl and HBr; or selected from the group that consists of HBr together with acetic acid, $H_3PO_3$ and $H_3PO_4$.

The present invention also relates to the product made from this process.

DETAILED DESCRIPTION OF PREFERRED EMBODIMENTS

N-phthalimido-GABA and N-phthalimido-GABA chloride are known (See GB 2,248,063 page 5 line 8–10, incorporated herein by reference). N-maleimido-GABA is also known [See J. Med. Chem., 18,1004,(1975), incorporated herein by reference].

According to the present invention in step (a) the compound of formula I is reacted with $H_3PO_3$

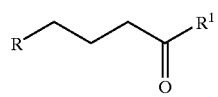

I wherein:
R is an imido group; and
$R^1$ is selected from the group which consists of chloro, bromo, iodo, fluoro, hydroxy, amino, $-OR^2$ or $-OC(O)R^2$, wherein $R^2$ is $C_1-C_{12}$ alkyl, $C_1-C_{12}$ cycloalkyl, or $C_1-C_{12}$ aryl;

In some cases, typically when $R^1$ is halogen, it is sufficient to react the compound of formula I with $H_3PO_3$ without the need to use an assisting agent. In other cases it is necessary to use one or more activating agents selected from the group which consists of $PCl_3$, $PCl_5$ and $POCl_3$.

As it will be seen in the examples, according to some embodiments of the present invention, the reaction of step (a) may be performed by using $H_3PO_3$ as a solvent. According to other embodiments, when a solidification problem occurs, a further solvent such as $H_3PO_4$ may be used in order to solve this problem.

In step (b), the product of step (a) is reacted with a deprotecting agent. The compound resulting from this step is alendronic acid.

The process of the present invention may be performed as a "one pot" process.

EXAMPLES

The following examples are given for the purpose of illustrating the present invention and shall not be construed as being limitations on the scope or spirit of the invention.

Example 1

A 100 ml nitrogen flushed flask fitted with a mechanical stirrer, reflux condenser and a thermometer, was charged with N-phthalimido-GABA chloride (4-phthalimidobutanoyl chloride, 8 g, 0.0318 mol, 1 eq) and phosphorous acid (5.2 g, 0.0635 mol, 2 eq.). The mixture was heated to 130° C. and kept at this temperature for 4 hours. 6N HCl (40 ml were added dropwise and the reaction mixture was refluxed for 18 hours. After cooling to 5° C. the phthalic acid was removed by filtration and the reaction mixture was distilled to dryness, ethanol (95%, 100 ml) was added, and alendronic acid was precipitated. The reaction mixture was refluxed for 1 hour and cooled to 25° C. Alendronic acid was collected by filtration, washed with 25 ml of 95% ethanol and dried in a vacuum oven to give 1.53 g (19.4%).

Example 2

A 100 ml nitrogen flushed flask fitted with a mechanical stirrer, a reflux condenser, a dropping funnel and a thermometer, was charged with N-phthalimido-GABA (4-phthalimidobutanoic acid, 8 g, 0.0343 mol, 1 eq) and phosphorous acid (14.06 Cr, 0.1715 mol, 5 eq.). The mixture was heated to 76° C. and phosphorous trichloride (6 ml, 0.0688 mol, 2 eq.) were added dropwise during 15 minutes. The reaction mixture was heated to 80° C. and kept at this temperature for 3 hours. 48% aqueous solution of HBr (40 ml) were added dropwise and the reaction mixture was refluxed for 18 hours. After cooling to 5° C. the phthalic acid was removed by filtration and the reaction mixture was distilled to dryness. Ethanol (95%, 100 ml) was added, and alendronic acid was precipitated. The reaction mixture was refluxed for 1 hour and cooled to 25° C. Alendronic acid was collected by filtration, washed with 25 ml of 95% ethanol and dried in a vacuum oven to give 3.25 g (38%).

Example 3

A 250 ml nitrogen flushed flask fitted with a mechanical stirrer, a reflux condenser, a dropping funnel and a thermometer, was charged with N-phthalimido-GABA (4-phthalimidobutanoic acid, 10 g, 0.0429 mol, 1 eq), phosphorous acid (5.3 g, 0.064 mol, 1.5 eq) and ortho-phosphoric acid (16.8 g, 0.01714 mol, 4 eq). The mixture was heated to 76° C. and phosphorous trichloride (7.5 ml, 0.0857 mol, 2 eq.) were added dropwise during 15 minutes. The reaction mixture was heated to 80° C. and kept at this temperature for 3 hours. A solution (70 ml) of 6N HCl was added dropwise and the and the reaction mixture was refluxed for 24 hours. After cooling to 5° C. the phthalic acid was removed by filtration and the reaction mixture was distilled to dryness. Ethanol (95%, 125 ml) was added, and alendronic acid was precipitated. The reaction mixture was refluxed for 1 hour and cooled to 25° C. Alendronic acid was collected by filtration, washed with 25 ml of 95% ethanol and dried in a vacuum oven to give 6.11 g (57%).

Example 4

A 100 ml nitrogen flushed flask fitted with a mechanical stirrer, a reflux condenser, a dropping funnel and a thermometer, was charged with N-maleimido-GABA (4-maleimidobutanoic acid, 5 g, 0.0273 mol, 1 eq) and phosphorous acid (11.2 g, 0.136 mol, 5 eq.). The mixture was heated to 76° C. and phosphorous trichloride (4.8 ml, 0.0546 mol, 2 eq.) were added dropwise during 15 minutes. The reaction mixture was heated to 80° C. and kept at this temperature for 16 hours. A mixture of 15 ml 48% aqueous solution of HBr and 15 ml glacial acetic acid was added dropwise and the reaction mixture was refluxed for 18 hours. After cooling to 5° C. the maleic acid was removed by filtration and the reaction mixture was distilled to dryness. Ethanol (95%, 100 ml) was added, and alendronic acid was precipitated. The reaction mixture was refluxed for 1 hour and cooled to 25° C. Alendronic acid was collected by filtration, washed with 25 ml of 95% ethanol and dried in a vacuum oven to give 1.43 g (21%).

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

We claim:

1. A process for the preparation of alendronic acid, which comprises the steps of:

a) reacting a compound of the formula I with $H_3PO_3$

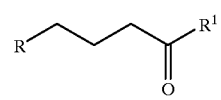

I wherein

R is an imido group; and $R^1$ is selected from the group which consists of chloro, bromo, iodo, fluoro, hydroxy, amino, $-OR^2$ or $-OC(O)R^2$, wherein $R^2$ is $C_1-C_{12}$ alkyl, $C_1-C_{12}$ cycloalkyl, or $C_1-C_{12}$ aryl;

b) reacting the product of step (a) with a deprotecting agent; and c) recovering alendronic acid.

2. A process according to claim 1 wherein R is selected from the group which consists of N-phthalimido and N-maleimido.

3. A process according to claim 1 wherein $R^1$ is selected from the group which consists of chloro, bromo and hydroxy.

4. A process according to claim 1 wherein step (a) further comprises the use of one or more of the compounds selected from the group which consists of $H_3PO_4$, $PCl_3$, $PCl_5$ and $POCl_3$.

5. A process according to claim 1 wherein step (b) comprises using one or more deprotecting agents selected from the group which consists of HCl, HBr, acetic acid, $H_3PO_3$, and $H_3PO_4$.

6. A process according to claim 1, wherein steps (a) and (b) take place in a single vessel.

7. A process according to claim 1 in which step (a) is performed at the temperature of between about 25° C. and about 180° C.

8. A process according to claim 7 in which step (a) is performed at the temperature of between about 80° and about 140° C.

9. A process according to claim 1 in which step (b) is performed at the temperature of between about 25° C. and about 130° C.

10. A process according to claim 9 in which step (b) is performed at the temperature of between about 100° C. and about 130° C.

11. A process according to claim 6 which is performed at the temperature of between about 25° C. and about 180° C.

12. A process according to claim 11 which is performed at the temperature of between about 80° C. and about 140° C.

13. A process according to claim 1 wherein the molar ratio between the compound of formula I and $H_3PO_3$ is between 1:1 and 1:6.

14. A process according to claim 13 wherein the molar ratio between the compound of formula I and $H_3PO_3$ is between 1:2 and 1:5.

15. A process according to claim 4 wherein the molar ratio between the compound of formula I and $PCl_3$ is between 1:1 and 1:6.

16. A process according to claim 15 wherein the molar ratio between the compound of formula I and $PCl_3$ is between 1:2 and 1:3.

17. A process according to claim 4 wherein the molar ratio between the compound of formula I and $H_3PO_4$ is between 1:1 and 1:6.

18. A process according to claim 17 wherein the molar ratio between the compound of formula I and $H_3PO_4$ is between 1:2 and 1:4.

19. A process according to claim 4 wherein the molar ratio between the compound of formula I and $PCl_5$ is between 1:1 and 1:6.

20. A process according to claim 19 wherein the molar ratio between the compound of formula I and $PCl_5$ is between 1:2 and 1:3.

21. A process according to claim 4 wherein the molar ratio between the compound of formula I and $POCl_3$ is between 1:1 and 1:6.

22. A process according to claim 21 wherein the molar ratio between the compound of formula I and $POCl_3$ is between 1:2 and 1:3.

* * * * *